United States Patent
Dabrowiak et al.

(10) Patent No.: US 11,253,392 B2
(45) Date of Patent: Feb. 22, 2022

(54) ENDOVASCULAR COOLING CATHETER SYSTEM WHICH EMPLOYS PHASE-CHANGING HEAT EXCHANGE MEDIA

(71) Applicant: ZOLL Circulation Inc., Sunnyvale, CA (US)

(72) Inventors: Jeremy Thomas Dabrowiak, Redwood City, CA (US); Frederick Faller, Burlington, MA (US)

(73) Assignee: ZOLL Circulation, Inc., San Jose, CA (US)

( * ) Notice: Subject to any disclaimer, the term of this patent is extended or adjusted under 35 U.S.C. 154(b) by 531 days.

(21) Appl. No.: 13/631,324

(22) Filed: Sep. 28, 2012

(65) Prior Publication Data
US 2013/0090708 A1    Apr. 11, 2013

Related U.S. Application Data

(60) Provisional application No. 61/540,439, filed on Sep. 28, 2011.

(51) Int. Cl.
*A61F 7/12*       (2006.01)
*A61F 7/00*       (2006.01)

(52) U.S. Cl.
CPC ........ *A61F 7/12* (2013.01); *A61F 2007/0056* (2013.01); *A61F 2007/126* (2013.01)

(58) Field of Classification Search
CPC ........ A61F 2007/0056; A61F 2007/126; A61F 7/12
See application file for complete search history.

(56) References Cited

U.S. PATENT DOCUMENTS

| | | | |
|---|---|---|---|
| 4,111,209 A * | 9/1978 | Wolvek | A61F 7/123 607/105 |
| 4,911,232 A | 3/1990 | Colvin et al. | |
| 6,149,677 A | 11/2000 | Dobak, III | |
| 6,301,904 B1 | 10/2001 | Goldstein | |
| 6,610,083 B2 | 8/2003 | Keller et al. | |
| 6,703,127 B2 | 3/2004 | Davis et al. | |
| 6,835,334 B2 | 12/2004 | Davis et al. | |
| 7,389,653 B2 | 6/2008 | Kasza et al. | |
| 2001/0007951 A1 | 7/2001 | Dobak, III | |
| 2003/0135252 A1* | 7/2003 | MacHold | A61M 25/10 607/106 |

(Continued)

FOREIGN PATENT DOCUMENTS

WO    WO2009/117586 A2    9/2009

OTHER PUBLICATIONS

International Search Report and Written Opinion for corresponding PCT/US2012/058015. International filing date Sep. 28, 2012.

(Continued)

*Primary Examiner* — Kaitlyn E Smith
*Assistant Examiner* — Yasamin Ekrami
(74) *Attorney, Agent, or Firm* — Fish & Richardson P.C.

(57) ABSTRACT

Devices and methods for cooling all or part of the body of a human or animal subject by inserting a heat exchange catheter into the subject's body and infusing into or through the catheter a heat exchange medium that contains liquid phase matter and frozen solid phase matter, wherein at least some of the solid phase matter melts while in the catheter.

38 Claims, 10 Drawing Sheets

(56) References Cited

U.S. PATENT DOCUMENTS

| | | |
|---|---|---|
| 2003/0222378 A1 | 12/2003 | Xing et al. |
| 2004/0050154 A1 | 3/2004 | Machold et al. |
| 2004/0076826 A1 | 4/2004 | Lee |
| 2005/0107006 A1* | 5/2005 | Makino .................. B24C 1/003 451/40 |
| 2005/0203598 A1* | 9/2005 | Becker ..................... A61F 7/02 607/105 |
| 2006/0161232 A1 | 7/2006 | Kasza et al. |
| 2007/0043409 A1* | 2/2007 | Brian, III .................. A61F 7/12 607/105 |
| 2007/0056313 A1* | 3/2007 | Kasza .................. A61F 7/0085 62/353 |
| 2007/0207186 A1* | 9/2007 | Scanlon .................... A61F 2/07 424/424 |
| 2008/0193653 A1 | 8/2008 | Oh |
| 2009/0043366 A1 | 2/2009 | Dae |
| 2009/0125087 A1 | 5/2009 | Becker et al. |
| 2009/0234325 A1* | 9/2009 | Rozenberg .............. A61F 7/123 604/514 |
| 2009/0255276 A1* | 10/2009 | Kasza ...................... F25C 1/00 62/68 |
| 2010/0324635 A1 | 12/2010 | Kreck |
| 2011/0022136 A1 | 1/2011 | Scott et al. |
| 2011/0088413 A1* | 4/2011 | Lampe .................. C09K 5/066 62/68 |
| 2011/0152680 A1* | 6/2011 | Kim .................... A61M 5/2053 600/432 |

OTHER PUBLICATIONS

Supplementary European Search Report for corresponding European patent application EP12835858.7.

* cited by examiner

ENDOVASCULAR COOLING CATHETER SYSTEM WHICH EMPLOYS PHASE-CHANGING HEAT EXCHANGE MEDIA

RELATED APPLICATION

This patent application claims priority to U.S. Provisional Patent Application No. 61/540,439 filed Sep. 28, 2011, the entire disclosure of which is expressly incorporated herein by reference.

FIELD OF THE INVENTION

This invention relates generally to devices and methods for medical treatment and more particularly to devices and methods for endovascular heat exchange for altering or controlling body temperature in a human or animal subject.

BACKGROUND OF THE INVENTION

Hypothermia can be induced in humans and some animals for the purpose of protecting various organs and tissues (e.g., hear, brain, kidneys) against the effects of ischemic, anoxic or toxic insult. For example, animal studies and/or clinical trials suggest that mild hypothermia can have neuroprotective and/or cardioprotective effects in animals or humans who suffer from ischemic cardiac events (e.g., myocardial infract, acute coronary syndromes, etc.), postanoxic coma after cardiopulmonary resuscitation, traumatic brain injury, stroke, subarachnoid hemorrhage, fever and neurological injury. Also, studies have shown that whole body hypothermia can ameliorate the toxic effects of radiographic contrast media on the kidneys (e.g., radiocontrast nephropathy) of patients with pre-existing renal impairment who undergo angiography procedures.

One method for inducing hypothermia is by endovascular temperature management (ETM) wherein a heat exchange catheter is inserted into a blood vessel and a thermal exchange fluid is then circulated through the heat exchange catheter. This technique can effectively cool blood flowing through the subject's vasculature and, as a result, lower the core body temperature of the subject to some desired target temperature. ETM is also capable of warming the body and/or of controlling body temperature to maintain a monitored body temperature at some selected temperature. If a controlled rate of re-warming or re-cooling from the selected target temperature is desired, that too can be accomplished by carefully controlling the amount of heat added or removed from the body and thereby controlling the temperature change of the patient.

In some situations, it is desirable to induce hypothermia rapidly. When blockage of an artery causes acute ischemia, such as is the case in acute myocardial infarction and ischemic stroke, a primary treatment objective is to reperfuse (i.e., restore blood flow to) the ischemic tissue within a short period of time (e.g., less than 5 hours) after the onset of acute clinical symptoms. Such reperfusion can be accomplished by surgery to remove or bypass the blockage or by catheter based interventions (e.g., angioplasty, stenting, atherectomy, catheter-based embolectomy, etc.) or through the use of thrombolytic drugs (e.g., tissue plasminogen activator (TPA) or streptokinase). It is currently believed that improved outcomes in such ischemic events may be achievable through the use of therapeutic hypothermia in combination with a reperfusion strategy such as surgery, catheter based intervention and/or thrombolytic drug therapy. For example, in one study, it was observed that the mean size of anterior wall myocardial infarctions is significantly reduced in patients whose core body temperature had been lowered to at least 35° C. prior to reperfusion of the infarct zone. This observation is not explained by other factors including time-to-presentation, lesion location and incidence of TIMI flow prior to angioplasty. Thus, evidence exists that the ability to induce hypothermia rapidly (i.e., prior to reperfusion) may be a critical factor in optimizing patient outcomes following acute ischemic events.

The present invention provides for rapid induction of hypothermia in ETM by using a heat exchange medium that undergoes an endothermic phase change as it circulates through the heat exchange catheter.

Matter primarily exists in four phases—solid, liquid, gas, and plasma—as well as a few other extreme phases such as critical fluids and degenerate gases. Generally, when a solid is warmed (or as pressure decreases), that solid will change to a liquid form and may eventually become a gas. For example, ice (frozen water) melts into liquid water when it is heated. As the water boils, the water evaporates and becomes water vapor. Sometimes, solids will transition directly from solid to gas, bypassing the liquid phase. This is known as sublimation.

Whenever a phase change occurs, energy is either absorbed or released. In exothermic phase changes, chemical potential energy is converted to heat energy, thereby resulting in a release of heat. In endothermic phase changes, heat energy is converted into chemical potential energy, thereby resulting in absorption of heat. Solid to liquid phase changes are typically endothermic.

The prior art has included certain heat exchange catheter systems wherein a volatile refrigerant is compressed to a liquid state, infused into a heat exchange catheter and allowed to expand within an expansion chamber, thereby undergoing an endothermic gas to liquid phase change. This gas to liquid phase change ostensibly results in absorption of heat to result in cooling of the subject's circulating blood and lowering of the subject's body temperature. Examples of heat exchange catheter systems wherein such gas-liquid phase change occurs are described in U.S. Pat. No. 6,149,677 (Dobak III, et al.), the entire disclosure of which is expressly incorporated herein by reference. The use of a compressed refrigerant to effect a gas to liquid phase change within an indwelling heat exchange catheter presents handling and processing issues as well as potential injury to the subject should the volatile refrigerant leak from the catheter into the subject's bloodstream.

There remains a need in the art for the development of new endovascular systems and methods for rapidly lowering a subject's body temperature in a safe and consistent manner.

SUMMARY OF THE INVENTION

Further details, aspects, elements and attributes of the present invention may be appreciated by those of skill in the art after reading the detailed description and examples set forth below.

In accordance with one aspect of the present invention, there is provided a heat exchange catheter or other body cooling device that is insertable into or positionable in contact with the body of a human or animal subject. Such catheter or other body cooling device has an inlet, an outlet and at least one lumen through which heat exchange medium may be circulated. The catheter is connected to a source of a heat exchange medium that comprises liquid phase matter and solid phase matter, wherein the solid phase matter has a melting point not higher than about 37 degrees C. and a pump or pressurization apparatus for circulating the heat exchange medium through the catheter or other body cooling device while it is inserted in or positioned on the body of a human or animal subject. During this process, at least some of the solid phase matter melts (i.e., undergoes a solid to liquid phase change), thereby removing heat from the heat exchange medium.

In accordance with another aspect of the present invention, there is provided a method for lowering the temperature of all or part of the body of a human or animal subject. Such method generally comprises the steps of A) positioning a heat exchange catheter or other heat exchange device in or on the subject's body; B) delivering into the catheter or other heat exchange device a flowable heat exchange medium such that it exchanges heat with the subject's body resulting in lowering of the temperature of all or part of the subject's body. The flowable heat exchange medium comprises solid phase matter that melts, either within the catheter or other heat exchange device or elsewhere within a heat exchange medium flow, path thereby removing heat from the heat exchange medium. The heat exchange medium does not directly contact or mix with any body fluid or tissue of the subject's body.

Further aspects, details, examples and embodiments of the invention will be appreciated by those of skill in the art upon reading the detailed description set forth below.

DETAILED DESCRIPTION OF THE DRAWINGS

DETAILED DESCRIPTION

The following detailed description, the accompanying drawings and the above-set-forth brief descriptions of the drawings are intended to describe some, but not necessarily all, examples or embodiments of the invention. The contents of this detailed description, the accompanying drawings and the above-set-forth brief descriptions of the drawings do not limit the scope of the invention, or the scope of the following claims, in any way.

Figure 1:
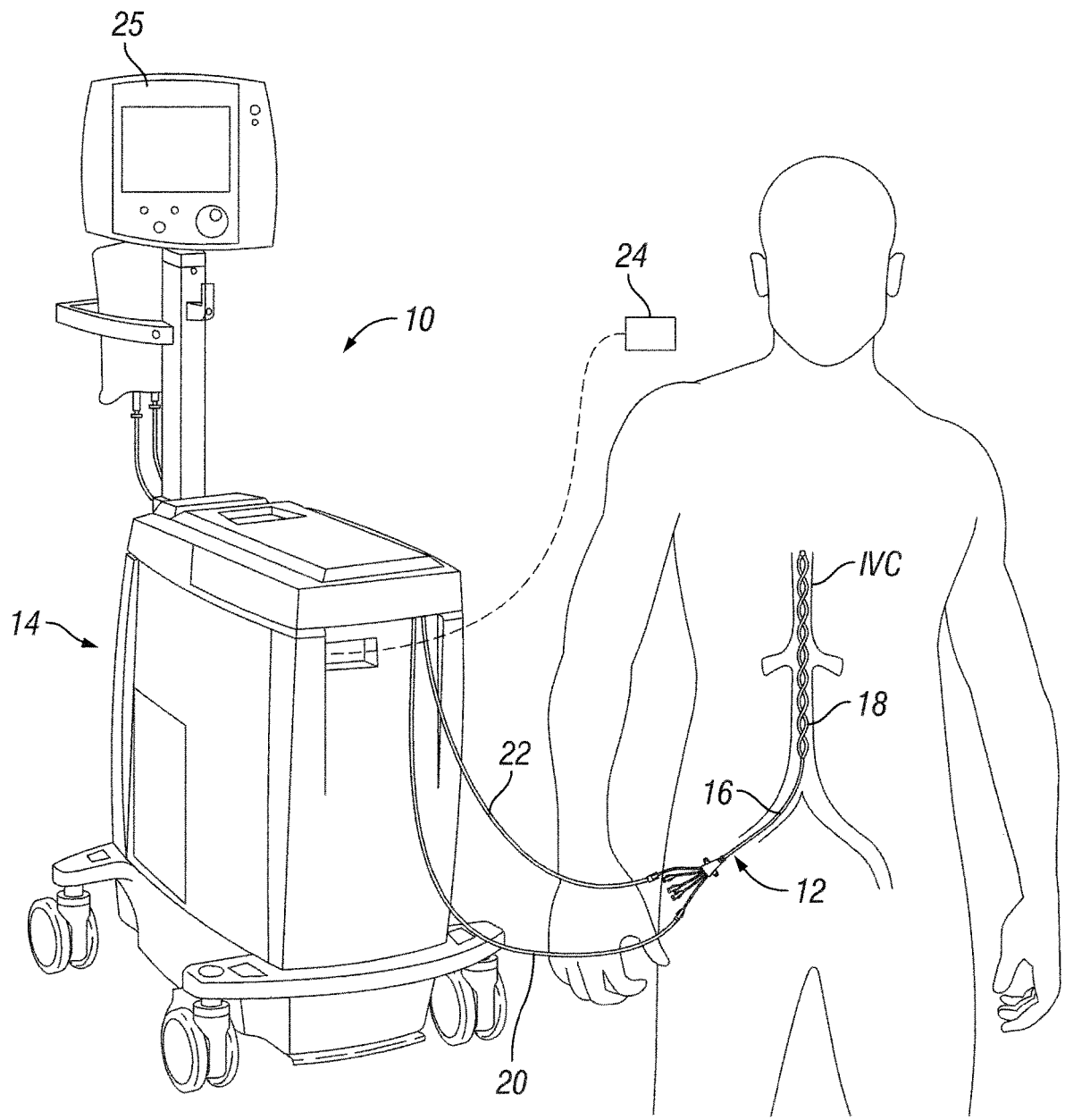
FIG. 1 is a general diagram of an endovascular heat exchange system of the present invention comprising an extracorporeal control console and a heat exchange catheter, wherein a distal portion of the heat exchange catheter is operatively inserted into the vasculature of a human subject.

General Aspects of a Heat Exchange Catheter System which Uses a Heat Exchange Slurry for Rapid Cooling of a Subject's Body FIG. 1 is a diagrammatic example of a body temperature management system 10 of the present invention. In this example, the body temperature management system 10 generally comprises a heat exchange catheter 12 that is connected to extracorporeal component(s) 14. A distal portion of the heat exchange catheter 16 is inserted into the vasculature of a human subject and positioned, in this example, so that a heat exchange region 18 of the catheter 16 is within the subject's inferior vena cava IVC. It is to be appreciated, however, that the catheter 16 and its heat exchange region 18 may be alternatively positioned in various other blood vessels, body lumens or body cavities, depending on the particular application and clinical setting in which the system is being utilized.

The extracorporeal component(s) 14 comprise, at minimum, a source of frozen solid/liquid heat exchange slurry and a pressure apparatus or pump for delivering that heat exchange slurry through inlet line 22 into an inflow lumen of the catheter 16. The solid-liquid heat exchange slurry then circulates through the catheter's inflow lumen and through a heat exchanger 18 on the catheter whereby the heat exchange slurry exchanges heat with blood flowing through the subject's vasculature. This exchange of heat causes some or all of the solid phase of the slurry to melt and causes cooling of the subject's flowing blood. This cooling of the subject's flowing blood results in cooling of downstream organ(s) (e.g., the heart or brain) and/or cooling of the subject's whole body. The melting of some or all of the solid particles contained in the heat exchange slurry results in substantially more cooling of the subject's flowing blood than would be attained using a liquid heat exchange medium that is devoid of solid phase particles which melt during the heat exchange. In this manner, the present invention cools target organ(s) or the whole body more quickly than the endovascular heat exchange systems of the prior art which utilized cooled liquid heat exchange media.

In at least some embodiments of the present invention, the heat exchange medium (including any remaining solid phase particles that have not melted) may be circulated back from an outflow lumen of the catheter 16, through return line 22, and into a container within the extracorporeal system 14. In this manner, any remaining solid particles may be circulated back through the catheter 16 alone or in combination with additional heat exchange slurry or temperature controlled liquid.

Composition and Preparation of Slurry

The heat exchange slurry may comprise any suitable mixture of frozen solid-phase particles and liquid-phase matter. Preferably, the heat exchange slurry will be sterile and sufficiently biocompatible to avoid serious injury to the subject if some or all of the slurry were to inadvertently leak from the catheter 12 into the subject's bloodstream or body. A slurry formed of frozen and liquid sodium chloride solution is one biologically compatible slurry that may be used in this invention. Examples of sterile saline slurries and their methods of manufacture are described in U.S. Pat. No. 7,389,653 (Kasza et al.) entitled Medical Ice Slurry Production Device, the entire disclosure of which is expressly incorporated herein by reference. In some applications of the present invention, such as those where relatively small diameter heat exchange catheters are used, it may be desirable for the solid particles of the slurry to be very small in diameter and/or for the slurry to contain a lubricious composition (e.g., a glycol such as propylene glycol) to deter agglomeration of the solid particles and/or to facilitate flow of the slurry through small diameter catheter lumens. Also, in at least some embodiments, it may be desirable for the solid particles of the slurry to be substantially spherical, or at least devoid of sharp edges, to facilitate flow of the slurry through small or tortuous catheter lumens.

Slurries useable in this invention may be prepared using known technology, such as a slurry ice generator having a scraped-surface vertical shell and tube heat exchanger. The inner surface of an inner tube is wiped using a wiping mechanism that comprises a sealed, rotating central shaft that has spring-loaded plastic blades or brushes extending outwardly from the shaft. Small ice crystals that form near the tube surface are wiped away from the surface by the rotating blades or brushes and are mixed with unfrozen liquid, thereby forming the slurry. Fluidized bed heat exchangers may also be used wherein steel particles circulate with the fluid to mechanically remove the crystals from the surface heat exchanger surface. The steel particles are then separated from the resultant ice slurry.

Another type of slurry generator that may be used is known as a direct contact slurry generator. In such device, an immiscible primary refrigerant is caused to evaporate in a manner that supersaturates water and forms small smooth ice crystals. However, a small amount of refrigerant may remain in ice crystals formed by this method.

Yet another type of slurry generator that may be used is known as a supercooling generator. In such device, water is pressurized and supercooled to −2° C. and then released through a nozzle. As it exits the nozzle, the supercooled water changes from liquid phase to solid phase, thereby forming small ice particles. In some embodiments, grinding or other In some embodiments, the heat exchange slurry may comprise phase change material (PCM) microcapsules disbursed in a liquid. Each PCM microcapsule comprises a core formed of phase changing material (e.g., frozen saline solution or other frozen liquid) and a shell which surrounds the core. PCM microcapsules have heretofore been reported to be useable in thermal management applications due to their ability to absorb and release large amounts of heat during phase change. Examples of PCM microcapsules and their methods of manufacture include, but are not limited to, those described in U.S. Pat. Nos. 4,911,232 (Colvin et al.); 6,703,127 (Davis, et al.) and 6,835,334 (Davis et al.) and United States Patent Application Publication Nos. 2003/0222378 (Xing et al.); 2004/0076826 (Lee et al.); 2004/0121072 (Xing et al.); 2006/0161232 (Kasza et al.); 20080193653 (Oh et al) and 2011/0008536 (Oh, et al), the entire disclosure of each such patent and published patent application being expressly incorporated herein by reference.

Figure 2:
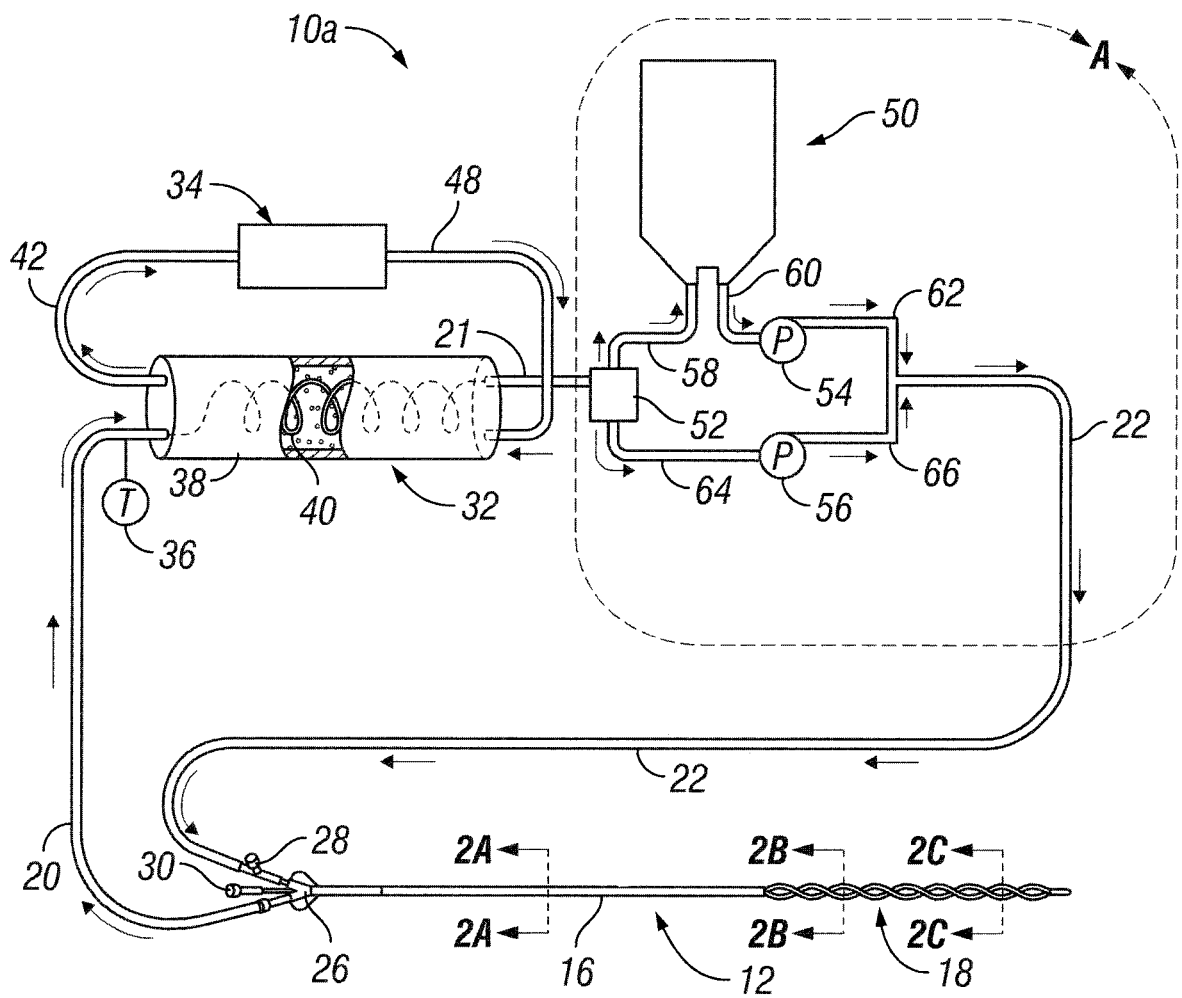
FIG. 2 is a schematic diagram on a first embodiment of a solid-liquid phase changing endovascular heat exchange system of the present invention.
Figure 3:
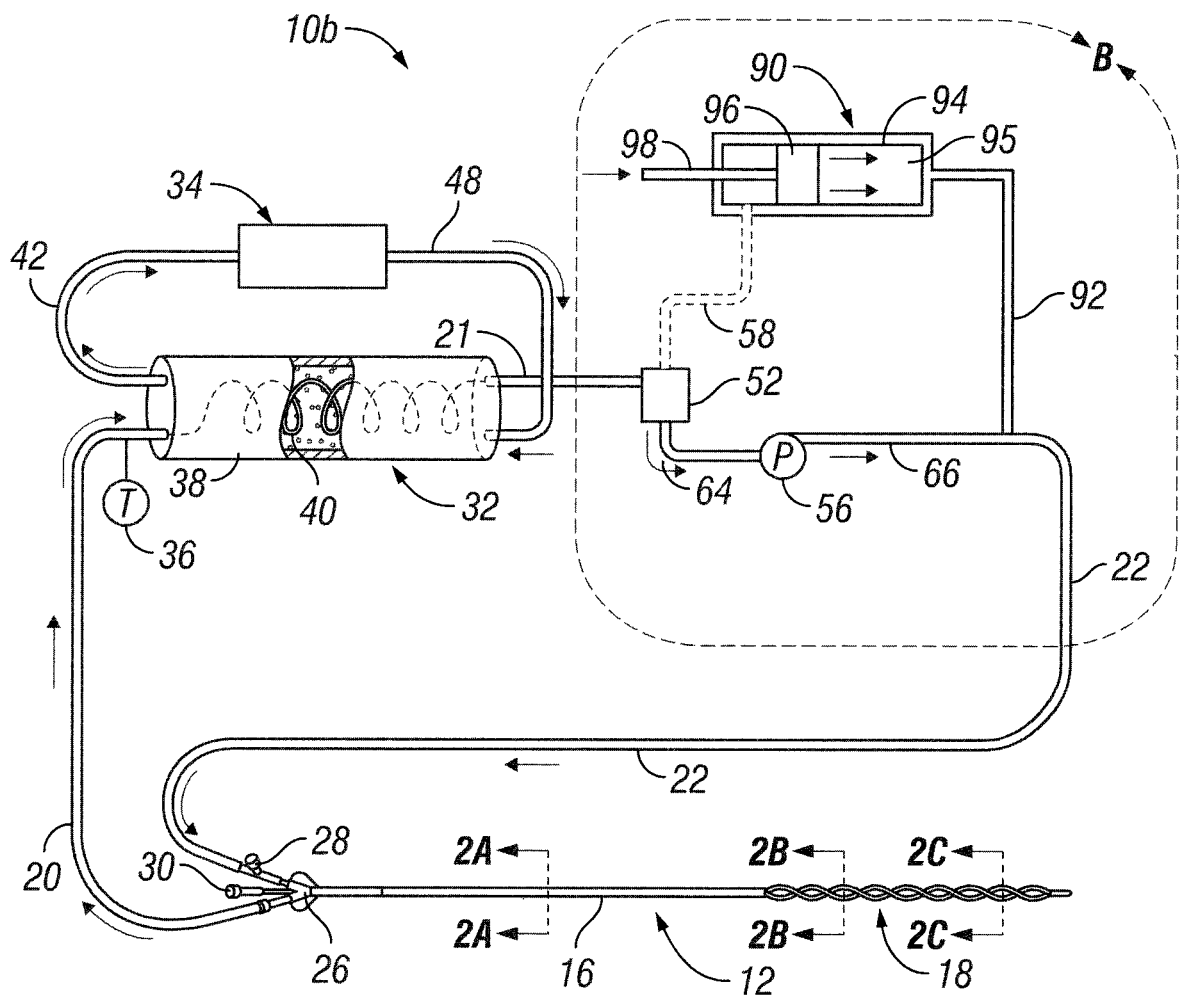
FIG. 3 is a schematic diagram of a second embodiment of a solid-liquid phase changing endovascular heat exchange system of the present invention.
Figure 4:
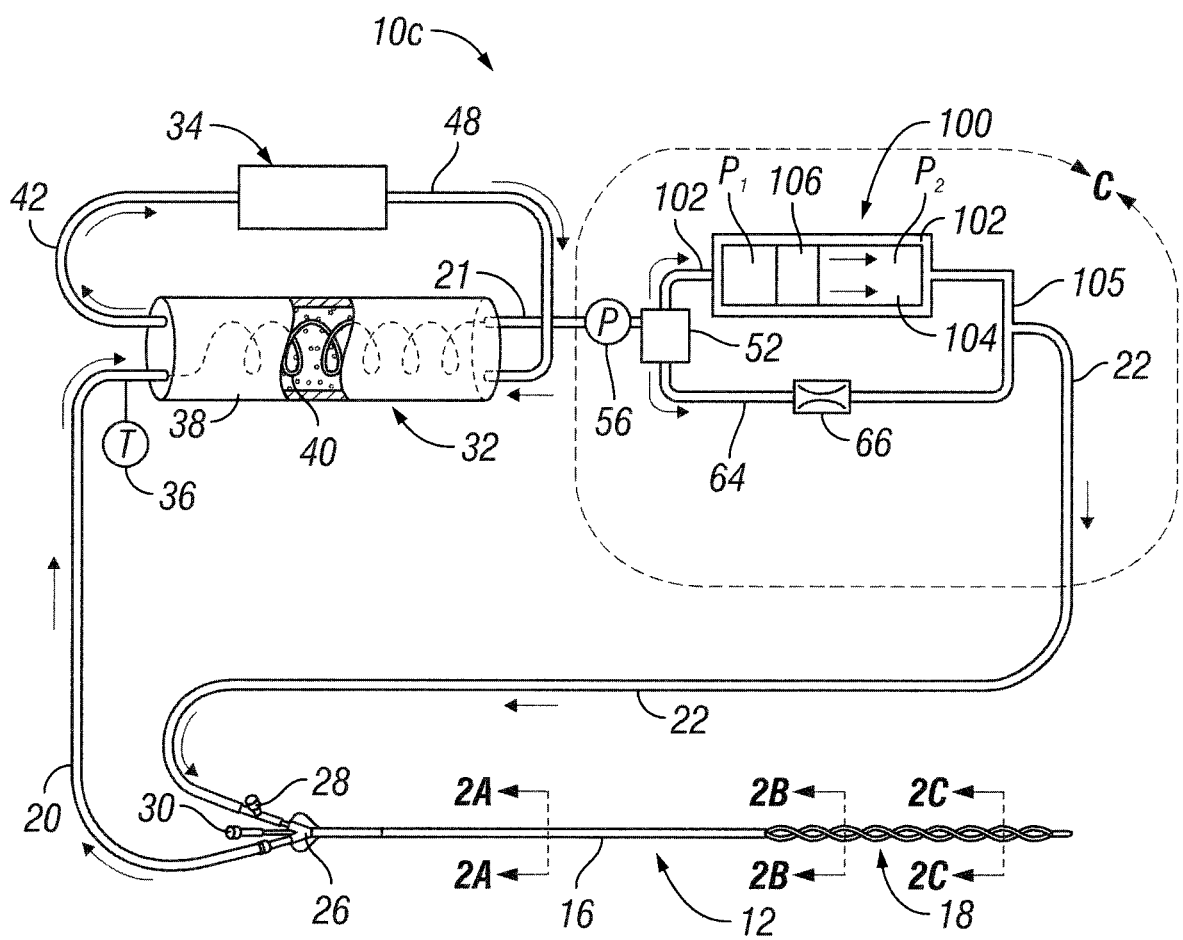
FIG. 4 is a schematic diagram of a third embodiment of a solid-liquid phase changing endovascular heat exchange system of the present invention.

Catheter Based Cooling of a Subject's Body Using the Solid-Liquid Heat Exchange Slurry The heat exchange slurry will typically be utilized for only an initial period of time or until the temperature of the organ(s) or whole body has been lowered to a target hypothermic temperature (e.g., 34-36 degrees C.). Thereafter, the system 10 may continue to control the temperature of the organ(s) or whole body by circulating a temperature controlled heat exchange liquid, such as 0.9% sodium chloride solution, through the catheter 16 in the same manner as heretofore accomplished by a number of commercially available endovascular heat exchange catheter systems, including the Thermogard XP Temperature Management System available from ZOLL Circulation of Sunnyvale, Calif. or the InnerCool RTx™ Endovascular System available from Philips Healthcare of Andover, Mass. In such embodiments, the extracorporeal system 14 may further comprise a cooler/heater for cooling or warming the heat exchange liquid, a pump for pumping that heat exchange liquid through the catheter 16, at least one temperature sensor 24 for sensing a body temperature of the subject, a user interface 25 by which a user may enter a desired target temperature and a controller, such as a computer or microprocessor, which receives the input target temperature, the sensed body temperature and, in response, controls the temperature and/or flow rate of the heat exchange liquid to attain and maintain the input target temperature. The slurry-delivering capacity may be integrated with the heat exchange fluid controlling/delivering capacity to achieve rapid initial cooling of a subject's body using the heat exchange slurry followed by maintenance of a desired target body temperature and eventual re-warming to normothermia using the traditional heat exchange liquid (e.g., saline solution). Specific examples of such systems are shown in FIGS. 2-7 and described herebelow. In the embodiments of FIGS. 2-4, a slurry concentrate is mixed with circulating heat exchange fluid to provide a slurry feed of suitable viscosity and having suitable solids content to be pumped through the particular catheter in use and to provide the desired amount of endovascular cooling. In the embodiments of 5 and 6 an in-line freezer device is used to form ice particles in the circulating heat exchange fluid. FIG. 7 shows an alternative catheter type that may be used in conjunction with any of the extracorporeal systems shown in FIGS. 1-6.

Figure 2A:
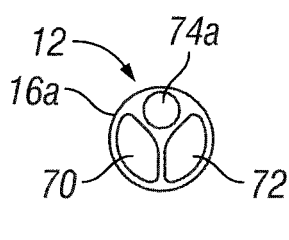
FIG. 2A is a cross sectional view through line 2A-2A of FIG. 2.
Figure 2B:
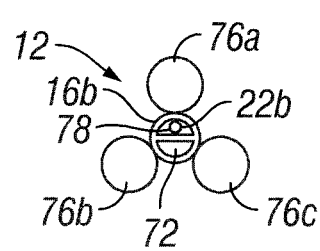
FIG. 2B is a cross sectional view through line 2B-2B of FIG. 2.
Figure 2C:
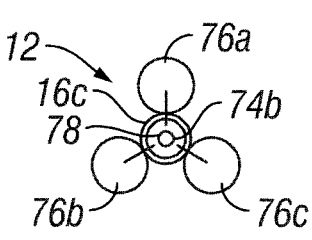
FIG. 2C is a cross sectional view through line 2C-2C of FIG. 2.

Examples of Endovascular Temperature Management Systems Equipped to Utilize Heat Exchange Slurry for Rapid Cooling of All or Part of a Subject's Body FIG. 2 shows one example of an endovascular temperature management system 10a of the present invention. In this particular example, the heat exchange catheter 12 comprises an elongate catheter body 16 having a heat exchanger 88 mounted on a distal portion of the catheter body 12. As shown in the cross sections of FIGS. 2A-2C, a proximal portion 16a of the catheter body comprises a flexible shaft having an inflow lumen 70, an outflow lumen 72 and a proximal working lumen segment 74a. A mid-portion 16b of the catheter body comprises a flexible shaft having shaft having the inflow lumen 70 and working lumen 74. A distal portion 16c of the catheter body has only the working lumen 74 passing therethrough. At or near the distal end of a proximal portion 16a of the catheter body, the outflow lumen 72 terminates and communicates through openings into the proximal ends of the three generally cylindrical balloon lobes 76a, 76b and 76c. At or near the distal end of the mid-portion 16b of the catheter body, the inflow lumen 70 terminates and communicates with the distal ends of the three generally cylindrical balloon lobes 76a, 76b and 76c. The balloon lobes 76a, 76b and 76c are helically twisted, wound or otherwise helically disposed about the mid-portion 16b of the catheter body. In this example, the mid-portion 16b of the catheter body comprises a continuation or extension of the inflow lumen 70 with a smaller tube connected to and forming an extension of the working lumen 74. The attachment of the balloon lobes to the catheter may be accomplished in any appropriate manner to accomplish the circulation of heat exchange fluid described here. One such method is described in detail in U.S. Pat. No. 6,610,083 (Keller, et al.), which patent is expressly incorporated herein by reference. The distal portion 16c of the catheter body extends beyond the distal ends of the balloon lobes 76a, 76b and 76c. The tube forming the mid-region extension of the working lumen 74 continues through this distal portion 16c of the catheter body and its lumen opens through an aperture in the distal tip of the catheter 12. Thus, in this manner, a continuous working lumen that extends through the entire length of the heat exchange catheter 12. However, it is to be appreciated that as an alternative, in some embodiments, a working lumen that runs less than the entire length of the catheter may be provided to facilitate rapid exchange of guidewires and/or catheters. Also, in some embodiments, the heat exchanger 88 may be formed at least in part of a heat transferring material selected from the group consisting of: polymers, metals, ceramics, polymer-metal composites, polymer metal mixtures, ceramic-metal composites, ceramic-metal mixtures and metalized ceramic material.

As those of skill in the art will appreciate, the working lumen 74 may facilitate advancement of the catheter 12 over a guidewire and/or to facilitate infusion of fluids (e.g., saline solution, therapeutic or diagnostic substances, radiographic contrast medium, aqueous oxygen, etc.) and/or to facilitate introduction of another catheter or apparatus into the subject's body. One example of another apparatus that may be advanced through the working lumen 74 is an endovascular embodiment of the body temperature measuring apparatus 24 (e.g., a catheter or wire having a temperature sensor that is advanceable out of the distal tip of the catheter 12 and useable for sensing the temperature of the subject's flowing blood). One example of an endovascular body temperature measuring apparatus that may be advanced through working lumen 74 is the Reprieve® endovascular temperature probe manufactured by ZOLL Circulation, Inc., Sunnyvale, Calif.

In typical operation when the catheter 12 is inserted via a femoral vein and the heat exchanger 18 is positioned within the inferior vena cava IVC (as shown in FIG. 1), the heat exchange medium (slurry or liquid) will flow distally through the inflow lumen 70, enter the distal ends of the balloon lobes 76a, 76b, 76c, flows in the proximal through the balloon lobes 76a, 76b, 76c, exit the proximal ends of the balloon lobes 76a, 76b, 76c into the outflow lumen 72 and then flow proximally trough the outflow lumen and out of the proximal end of the catheter 12.

In this system 10a, the extracorporeal components comprises an extracorporeal heat exchanger 32, a heater/cooler device 34 an air separator 52 and a a vessel 50 which contains a concentrated slurry. An outflow tube 20 connects the outflow lumen 72 the catheter 12 to an inner tube 40 of the heat exchanger 32. A temperature sensor 36 may optionally be provided to sense the temperature of heat exchange fluid returning from the catheter 12 before it enters the extracorporeal heat exchanger 32. Tubes 42 and 48 connect the heater/cooler device 34 to the shell 38 of the extracorporeal heat exchanger 32 to circulate fluid of a desired temperature through the shell 38. The outlet end of the heat exchanger tube 40 is connected to air separator 52 by way of tube 21. Thus, heat exchange fluid that returns from the catheter is passed through the heat exchanger tube 40 where its temperature is adjusted as desired and then into air separator 52. Air removed by the air separator is vented through tube 58 into the slurry-containing vessel 50 or alternatively into the atmosphere. Liquid (with any entrained ice particles) travels from the air separator 52, through tube 64 to pump 56. Slurry travels from the slurry containing vessel 50 through tube 60 to pump 54. Pumps 54 and 56 are operated to pump the desired ratio of slurry concentrate and liquid through lines 62 and 66, respectively so that they become combined in inflow line 22. This forms the desired heat exchange slurry which is delivered through inflow line 22, into inflow lumen 70 of the catheter 12 such that it circulates through the catheter 12 in the above-described manner. After all or part of the subject's body has been cooled to the desired hypothermic temperature, the slurry pump 54 may be turned off and the system will continue to operate in maintenance mode using only liquid heat exchange medium without solid ice particles.

Figure 2D:
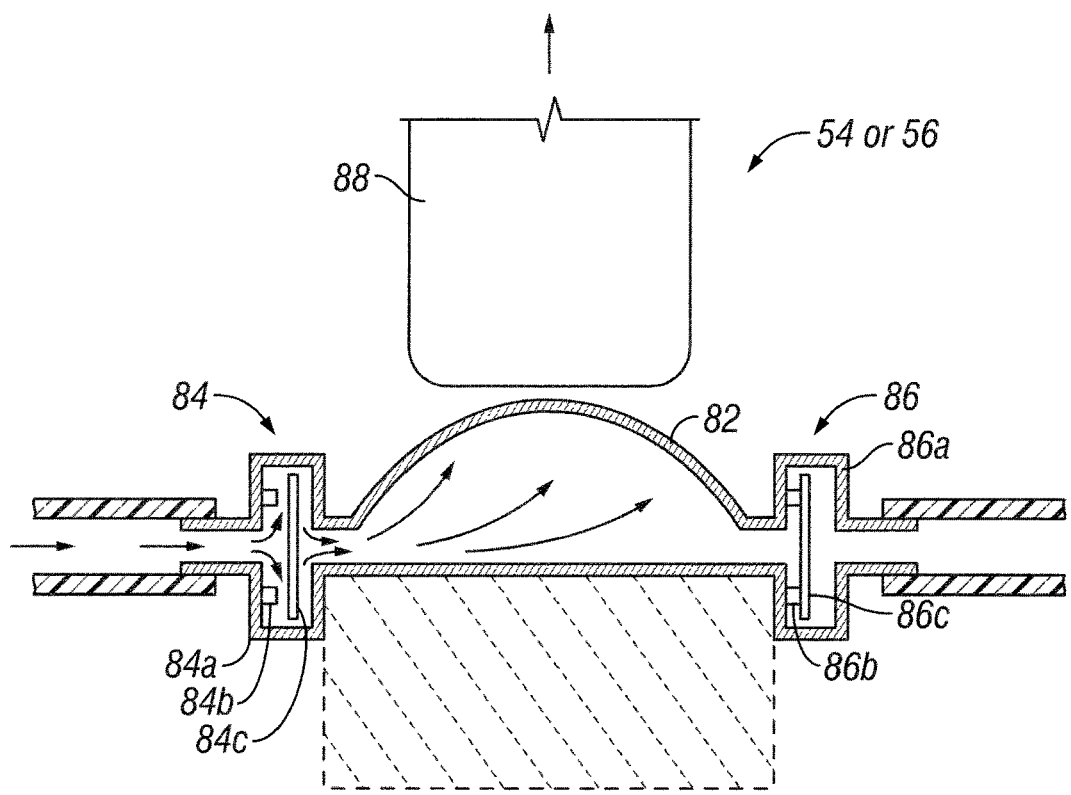
FIGS. 2D and 2E are schematic diagrams of one non-limiting example of a pump that may be used for pumping slurry in the system of FIG. 2 or any other system of the present invention which incorporates a slurry pump.
Figure 2E:
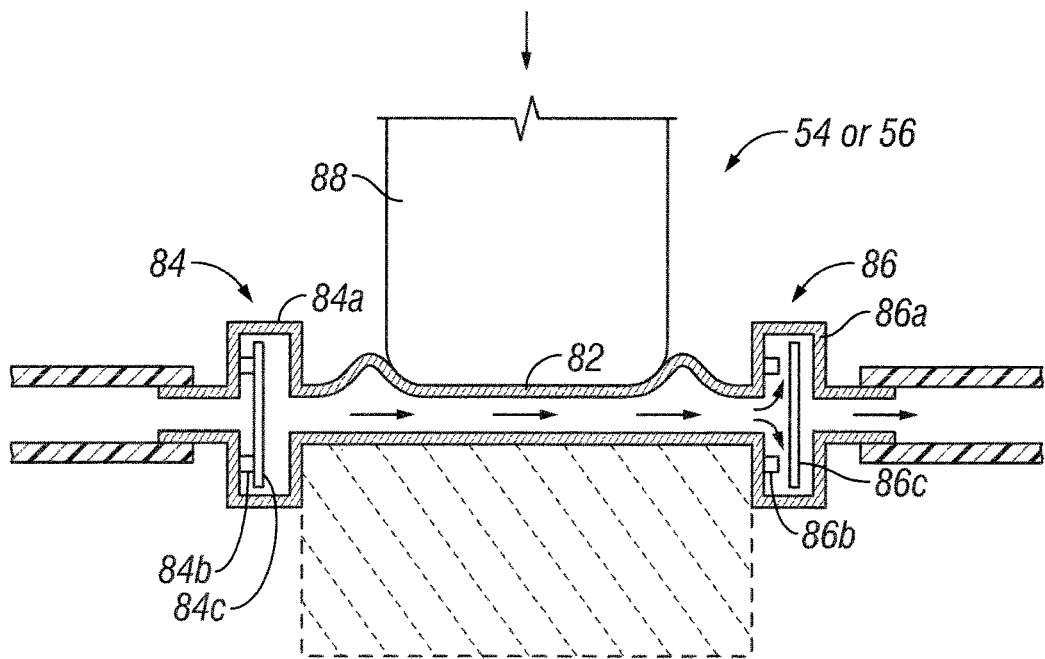

The slurry pump 54 will be of a type that is capable of reproducibly pumping a metered volume of the relatively thick slurry concentrate. One example of such a pump is shown schematically in FIGS. 2D and 2E. In this non-limiting example, the pump comprises a collapsible dome diaphragm 82, an upstream check valve 84 located upstream of the dome diaphragm 82 and a downstream check valve 86 located downstream of the dome diaphragm 82. The check vales 84, 86 may be any suitable type(s) of check valves, including but not necessarily limited to ball check vales, diaphragm check valves, swing check valves, tilting disc check valves, stop check valves, lift check valves, clapper check valves, wafer check valves, duckbill check valves, electrically actuated check valves, etc. The upstream check valve 84 opens, the downstream check valve 86 closes and the dome diaphragm 82 assumes a non-compressed shape when the ram 88 cycles to its retracted position shown in FIG. 2D. This causes slurry to flow through the upstream check valve 84 into the inner cavity of the dome diaphragm 82. Then, when the ram 88 cycles to its advanced position as shown in FIG. 2E, the upstream check valve 84 closes, the downstream check valve 86 opens and the dome diaphragm 82 becomes compressed, thereby expelling slurry that has accumulated within the interior of the dome diaphragm 82 through the downstream check valve 86. In this manner, reciprocating motion of the ram 88 causes slurry to be pumped through the circuit. In the particular non-limiting example shown, each check valve 84, 86 comprises a rigid housing 84a, 86a which defines a flow chamber therewithin, a moveable diaphragm 84c, 86c and a seal ring 84b, 86b located on the inner wall of the housing on the upstream side of each diaphragm 84c, 86c. As shown, when the ram 88 is retracted and the dome diaphragm moves to its non-collapsed configuration, the valve diaphragms 84c and 86c are drawn inwardly, causing the upstream diaphragm 84c to separate away from the adjacent seal ring 84b (thereby opening the upstream check valve 84) and causing the downstream valve diaphragm 86c to seat firmly against the adjacent seal ring 86b (thereby closing the downstream check valve 86 to close. The speed at which the ram member 88 reciprocates will dictate the slurry concentrate throughput rate of this pump 54.

FIG. 3 shows another example of an endovascular temperature management system 10b of the present invention. In this example, the system 10b incorporates a catheter 12, extracorporeal heat exchanger 32 and heater cooler 34 and interconnecting conduits 20, 22, 42, 48 of the same type as described above with respect to FIG. 2. However, this system 10b differs from the showing of FIG. 2 in that portion B of this system 10b replaces portion A of the system 10a seen in FIG. 2.

Portion B of system 10b combines a slurry concentrate with a diluent fluid (e.g., heat exchange fluid that has returned from the catheter 12) to form a heat exchange slurry that is then circulated through the catheter 12. As shown, the outlet end of the extracorporeal heat exchanger tube 40 is connected to air separator 52 by way of tube 21. Heat exchange medium returning from the catheter 12 (with or without any remaining frozen particles) passes through the heat exchanger tube 40 where its temperature may be adjusted as desired and then into air separator 52. Air removed by the air separator 52 is vented through tube 58. The remaining heat exchange liquid (with any remaining ice particles that did not melt during the prior circulation through the circuit) is pumped by pump 56 through line 64 and into line 66. The slurry concentrate injector 90 comprises a housing 94 having an enclosed inner cavity 95 that contains a slurry concentrate, a piston 96 which is in substantially sealing contact with the inner wall of the cavity 95 and a drive 98 for driving the piston 96. As the drive 98 advances the piston 96, the piston 96 forces slurry concentrate out of the injector's inner cavity 95 through line 92. The piston drive 95 may be manual, machine-driven, hydraulic, gas-driven or may be driven in any other suitable manner that causes the piston 96 to advance at a desired rate or rates to thereby deliver desired ratio(s) of slurry concentrate to be combined with the circulating heat exchange liquid. Line 92 joins with line 66 such that the heat exchange liquid flowing through line 66 combines with slurry concentrate flowing though line 92, thereby creating heat exchange slurry of a desired consistency in inflow line 22. This heat exchange slurry then flows through inflow line 22 and circulates through the catheter 12 in the manner described above.

FIG. 4 shows another example of an endovascular temperature management system 10b of the present invention. In this example, the system 10c incorporates a catheter 12, extracorporeal heat exchanger 32, a heater/cooler 34 and interconnecting conduits 20, 22, 42, 48 of the same type as described above with respect to FIG. 2. However, this system 10c differs from the showing of FIG. 2 in that portion C of this system 10c replaces portion A of the system 10a seen in FIG. 2.

Portion C of system 10c uses a pressure driven piston system to combine a slurry concentrate with a circulating heat exchange medium (e.g., heat exchange medium that has circulated through and returned from the catheter 12) to form a desired heat exchange slurry that is then circulated through the inflow line 22 and into the catheter 12. As shown, pump 56 pumps chilled heat exchange medium (with or without any remaining frozen particles) saline through the heat exchanger outlet line 21 into air separator 52. Air removed by the air separator 52 (and potentially a quantity of overflow heat exchange medium) is vented through a vent tube 102 into a slurry concentrate injector 100 on the left side of the piston 106. The remaining heat exchange liquid (with any remaining ice particles that did not melt during the prior circulation through the circuit) flows through line 64 and through flow restrictor 66. The flow restrictor 66 may be adjustable to control the amount of back pressure in line 64 and the amount of overflow heat exchange medium that flows through vent tube 102 and into the slurry concentrate injector 100 on the left side of the piston 106. The slurry concentrate injector 100 comprises a housing 102 having an enclosed inner cavity 104 that contains a slurry concentrate on the right side of piston 106. The piston 106 is in substantially sealing slidable contact with the inner wall of the cavity 104. As air and overflow heat exchange medium passing through vent line 102 accumulates on the left side of the piston 106 the pressure $P_1$ on the left side of the piston will rise. When the pressure $P_1$ on the left side of the piston 106 exceeds the pressure $P_2$ on the right side of the piston 106, the piston 106 will advance as indicated by arrows on FIG. 4. Such advancement of the piston 106 in response to the incoming air forces slurry concentrate out of the injector's inner cavity 104 through line 105. Line 105 joins with line 64 such that the heat exchange liquid flowing through line 64 combines with slurry concentrate flowing though line 104, thereby creating heat exchange slurry of a desired consistency in inflow line 22. This heat exchange slurry then flows through inflow line 22 and circulates through the catheter 12 in the manner described above. The amount of flow restriction caused by the flow restrictor 66 may be adjusted to result in the desired heat exchange slurry consistency (i.e., the desired ratio of ice particles to liquid). In this or any embodiments of the present invention, an automated microprocessor, computer or other controller may receive signals from a sensor (see FIGS. 9A and 9B) which senses the consistency of the heat exchange slurry flowing through inflow line 22. In response, such microprocessor, computer or other controller may issue control signals to other components of the system to change the relative amounts of ice particles and liquid in that heat exchange slurry. In this particular embodiment, such microprocessor, computer or other controller may be programmed to issue control signals to the fow restrictor 66 to adjust the amount of flow allowed through the flow restrictor 66 in a manner that results in the desired heat exchange slurry consistency in line 22 (i.e., the desired ratio of ice particles to liquid).

Figure 5:
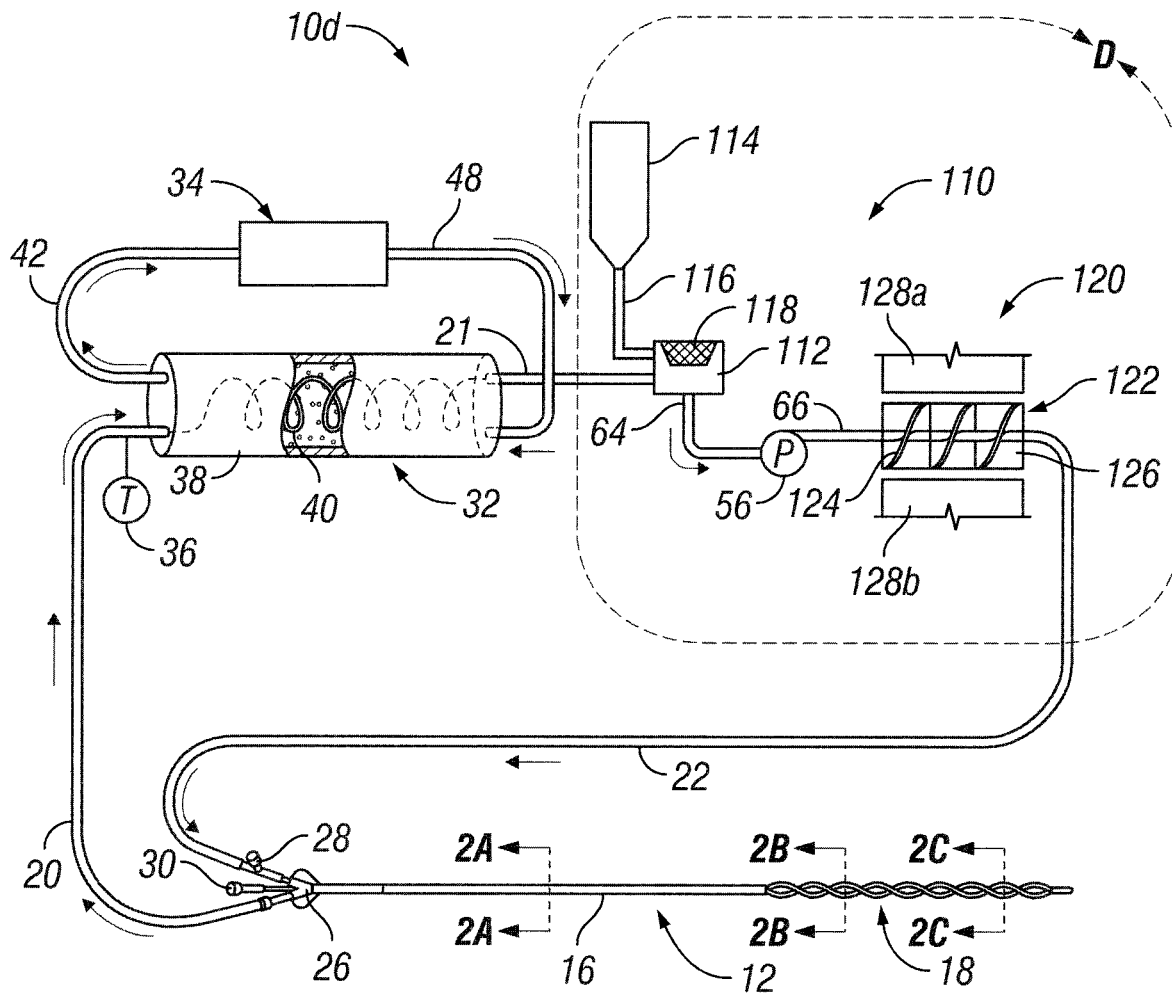
FIG. 5 is a schematic diagram of a fourth embodiment of a solid-liquid phase changing endovascular heat exchange system of the present invention.

FIG. 5 shows another example of an endovascular temperature management system 10d of the present invention. In this example, the system 10d incorporates a catheter 12, extracorporeal heat exchanger 32 and heater cooler 34 and interconnecting conduits 20, 22, 42, 48 of the same type as described above with respect to FIG. 2. However, this system 10d differs from the showing of FIG. 2 in that portion D of this system 10d replaces portion A of the system 10a seen in FIG. 2. In this system 10d, no slurry is required to be prepared offline. Instead, a fluid source, such as a bag of liquid saline 114, is spiked or otherwise connected to the system 10d and a freezer device, such as a disposable slurry generator 120, is used to form a desired amount of frozen solid matter in the circulating heat exchange liquid. In the embodiment shown, the outlet end of the extracorporeal heat exchanger tube 40 is connected to an air separator 112 by way of tube 21. Heat exchange medium returning from the catheter 12 (with or without any remaining frozen particles) passes through the heat exchanger tube 40 where its temperature may be adjusted as desired and then into air separator 112. Air removed by the air separator 112 is vented through tube a hydrophobic membrane 118. Additional heat exchange liquid (e.g., saline solution) from bag 114 passes through line 116 and into air separator 112 to combine with the remaining liquid and to make up for the volume of gas that has been vented through hydrophobic membrane 118. The heat exchange liquid (with any remaining ice particles that did not melt during the prior circulation through the circuit) is pumped by pump 56 through lines 64 and 66 and into slurry generator 120. It is to be appreciated, however, that the extracorporeal heat exchanger 32 and heater/cooler 34 are optional components of this system. If such optional components were eliminated from the system, the heat exchange medium returning from the catheter 12 via return line 20 would flow directly into line 21 and into the air separator 112.

Figure 5A:
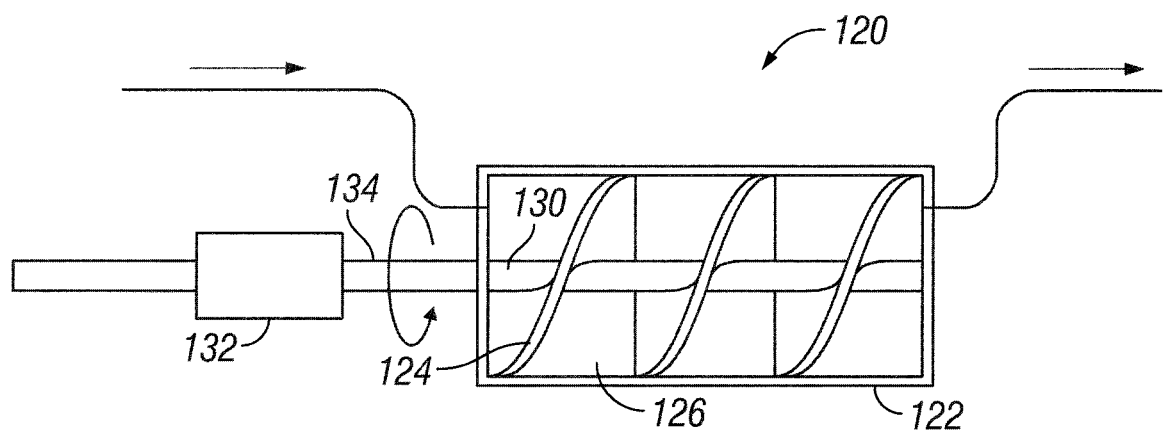
FIG. 5A is a schematic sectional diagram of one non-limiting example of a slurry generating device useable in the system of FIG. 5 or any other system of the present invention which incorporates a slurry generating device.
Figure 5B:
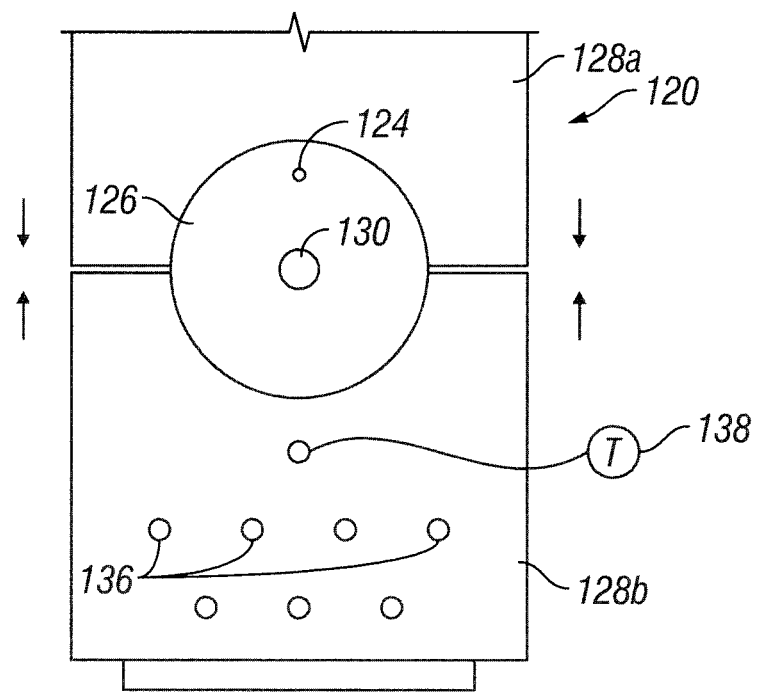
FIG. 5B is a schematic sectional diagram of a slurry generating device of FIG. 5A positioned between cooling elements.

FIGS. 5A and 5B show additional details of the slurry generator 120 used in this example. The slurry generator 120 comprises an enclosed generally cylindrical vessel 122 having a sealed rotating shaft 130 extending thereinto. A generally round scraper 126 is attached to the shaft 130. The rotation of the shaft may be driven by a variable speed electric motor 132 or any other suitable means. Chiller(s), such as refrigerated block members 128a, 128b having refrigeration coils 136 therein, are positioned adjacent to the vessel 122 to cool the walls of the vessel 122 to a temperature which causes the heat exchange liquid to freeze when it contacts the inner wall of the vessel 122. The refrigerated block members 128a, 128b may be reuseable and the vessel 122, shaft 130 and scraper 124 may be disposable. The refrigerated block members 128a, 128b may be moveable away from each other to allow removal and replacement of the disposable vessel 122/shaft 130/scraper 124 unit and then the refrigerated block members 128a, 128b may be moveable back toward each other to surround or abut the outer surface of the vessel 122, thereby providing for efficient heat exchange between the refrigerated block members 128a, 128b and the wall of the vessel 122. During operation, the rotating scraper 124 separates formed particles of frozen matter from the vessel wall, causing such particles of frozen matter to become combined with unfrozen liquid (and any residual frozen particles that did not melt during a prior circulation through the catheter 12) flowing through the vessel 122. This forms the desired heat exchange slurry having the desired ratio of frozen solid particles to liquid. This heat exchange slurry then exits the vessel 122 and flows through inflow line 22 and circulates through the catheter 12 in the manner described above.

The rate of ice formation in the slurry generator 120 may be controlled by adjusting the amount of cooling applied to the wall of the vessel 122 and/or the speed of the scraper 124. Temperature feedback may be used to adjust the rate of ice formation to optimize the saline return temperature and, possibly, to ensure that the amount of any ice particles remaining in the recirculated heat exchange medium is not more than can be suitably pumped by the pump 56. To facilitate this, or more temperature sensor(s) 138 may optionally be provided to sense the temperature of the refrigerated block members 128a, 128b and/or the temperature of the wall of the vessel 122. A controller may be programmed to receive the temperature(s) sensed by such temperature sensor(s) and to modify, in response, the temperature of the vessel 122 and/or the flow rate of heat exchange fluid delivered by the pump 56 and/or the rate of rotation of the scraper 124, as needed, to control the amount of frozen solid phase matter in the heat exchange slurry.

Figure 6:
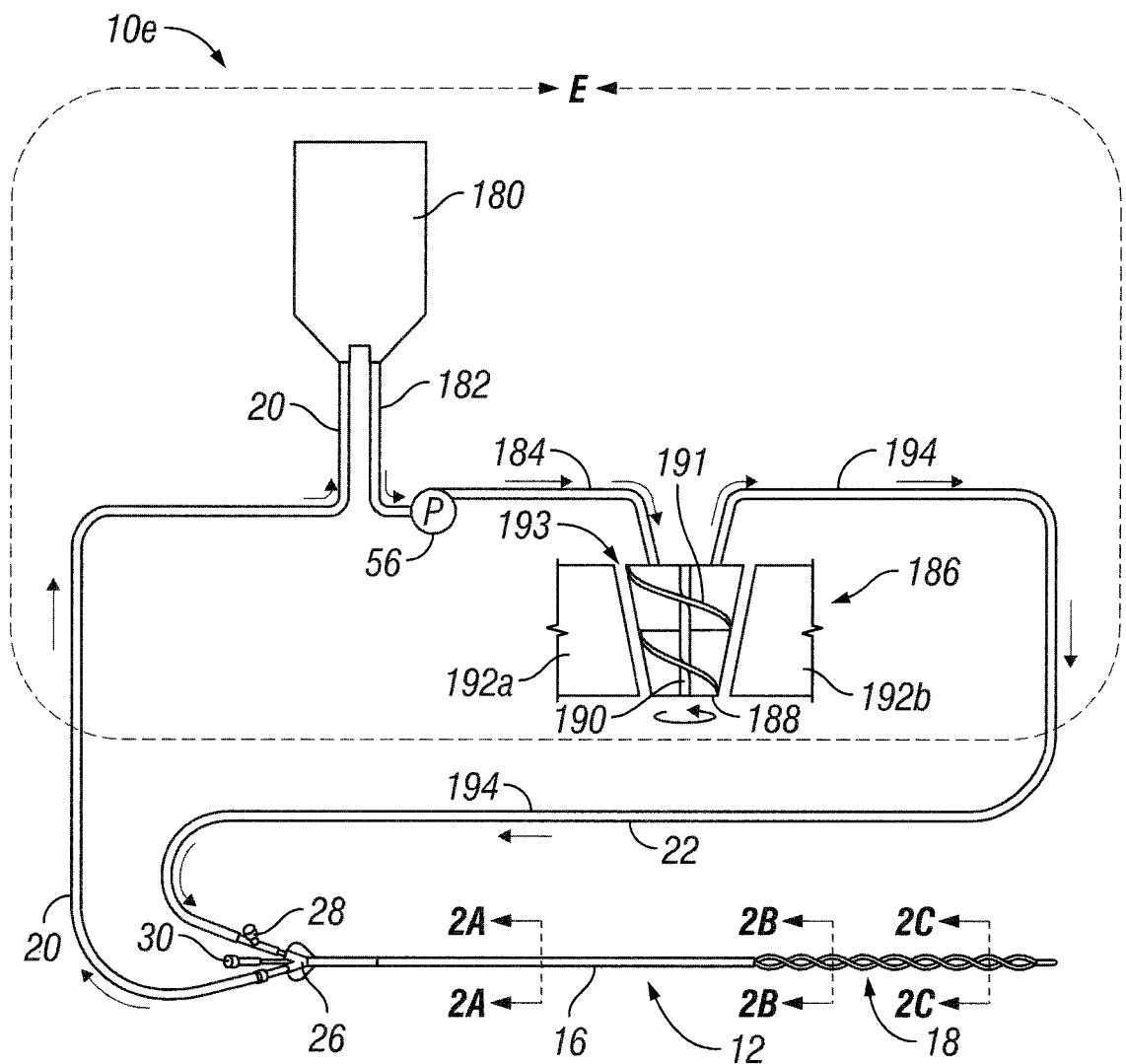
FIG. 6 is a schematic diagram of a fifth embodiment of a solid-liquid phase changing endovascular heat exchange system of the present invention.
Figure 7:
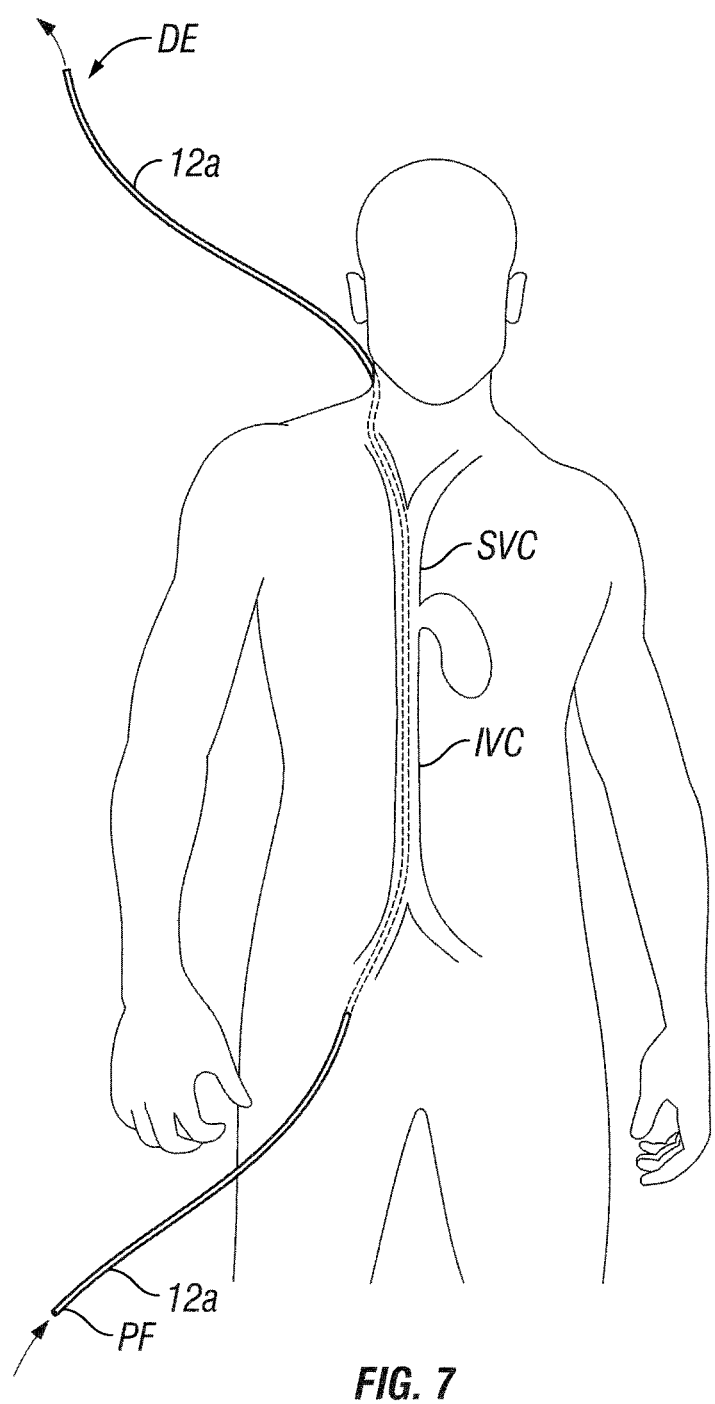
FIG. 7 is a schematic drawing of a human subject having an alternative heat exchange catheter inserted in the subject's body.

FIG. 6 shows another example of an endovascular temperature management system 10e of the present invention. In this example, the system 10e incorporates a catheter 12 and interconnecting conduits 20, 22 of the same type as described above with respect to FIG. 2. However, this system 10e differs from the showing of FIG. 2 in that portion E of this system 10e replaces portion A of the system 10a seen in FIG. 2 and the extracorporeal heat exchanger 32 and heater cooler 34 and interconnecting conduits 42, 48 are not present, but may optionally be included. In this system 10e, no slurry is required to be prepared offline. A reservoir 180, such as a bag of liquid saline solution 180 or other container, is connected to the return line 20 which returns heat exchange medium from the catheter (including any particles of frozen solid phase matter that did not melt while circulating through the catheter 12) and to an outlet line 56. The returning heat exchange medium (including any residual frozen solid phase matter) flows from return line 20 and into reservoir 180, where it combines with any heat exchange medium that is already present in the reservoir 180. In some embodiments, the reservoir 180 may be compliant or may include an air vent to allow separation of air for the liquid (and any residual solid phase matter). Heat exchange medium then flows out of the reservoir 180 through line 182, through pump 56, through line 184 and into slurry generator 186, where a portion of the liquid phase becomes frozen to form a heat exchange slurry of a desired solid/liquid consistency.

In the system 10d of FIG. 6, the slurry generator 186 comprises an enclosed generally frustoconical vessel 188 having a sealed rotating shaft 190 extending thereinto. A generally round scraper 191 of tapered diameter is attached to the shaft 190. The rotation of the shaft 188 may be driven by a variable speed electric motor (not shown) or any other suitable means. Chiller(s), such as one or more refrigerated block member(s) 192a, 192b, define a tapered cavity 193. The vessel 188, with its shaft 191 and scraper 190 positioned therein, is insertable in the tapered cavity 193, without necessarily requiring movement of the refrigerated block member(s) 192a, 192b. When the vessel 188 is positioned within the tapered cavity 193, the wall of the vessel will be in abutment with or in heat exchange proximity to the refrigerated block member(s) 192a, 192b. In this manner, the refrigerated block member(s) 192a, 192b will cool the wall of the vessel 188. During operation, the rotating scraper 191 separates formed particles of frozen matter from the wall of the vessel 188, causing such particles of frozen matter to become combined with unfrozen liquid flowing through the vessel 188. This forms the desired heat exchange slurry having the desired ratio of frozen solid particles to liquid. This heat exchange slurry then exits the vessel 188 through line 194. Line 194 is connected to the inflow line 20 through which the slurry then flows into, and circulates through, the catheter 12 in the above-described manner.

As in other embodiments, the rate of ice formation in this slurry generator 186 may be controlled by adjusting the amount of cooling applied to the wall of the vessel 188 and/or the speed of the scraper 191. Temperature feedback may be used to adjust the rate of ice formation to optimize the saline return temperature and, possibly, to ensure that the amount of any ice particles remaining in the recirculated heat exchange medium is not more than can be suitably pumped by the pump 56. To facilitate this, or more temperature sensor(s) (not shown in FIG. 6) may optionally be provided ate one or more location(s) in the system 10e to sense the temperature of the refrigerated block members 128a, 128b and/or the temperature of the wall of the vessel 122 and/or the temperature of the heat exchange medium. A controller may be programmed to receive the temperature(s) sensed by such temperature sensor(s) and to modify, in response, the temperature of the vessel 188 and/or the flow rate of heat exchange fluid delivered by the pump 56 and/or the rate of rotation of the scraper 124, as needed, to control the amount of frozen solid phase matter in the heat exchange slurry.

It is to be appreciated that, the catheter through which the heat exchange slurry is circulated need not be the specific catheter 12 shown and described in the above-set-forth examples, but rather, may be any suitable catheter by which heat exchange may occur between the heat exchange slurry and the subject's body or flowing blood without causing the slurry to directly contact or mix with any body fluid or tissue of the subject's body. Some catheters may be capable of use with more concentrated slurries than others because of limitations in the size or configuration of the catheter lumen(s) or other aspects of the catheter construction. Also, the heat exchange slurry need not necessarily circulate in and out of the same end of the catheter. Rather, as shown in FIG. 7, in some embodiments the proximal and distal ends PE, DE of the catheter 12a may both be exteriorized while a portion of the catheter between the ends PE, DE extends through the subject's vasculature or body. In this manner, the heat exchange slurry may enter one end DE or PE of the catheter 12a and may exit the other end De, PE. Examples of various heat exchange catheters that may be used in connection with this invention include those commercially available from ZOLL Circulation, Inc. of Sunnyvale, Calif. and Koninklijke Philips Electronics N.V./Phillips Healthcare (InnerCool), Andover, Mass.

Figure 8:
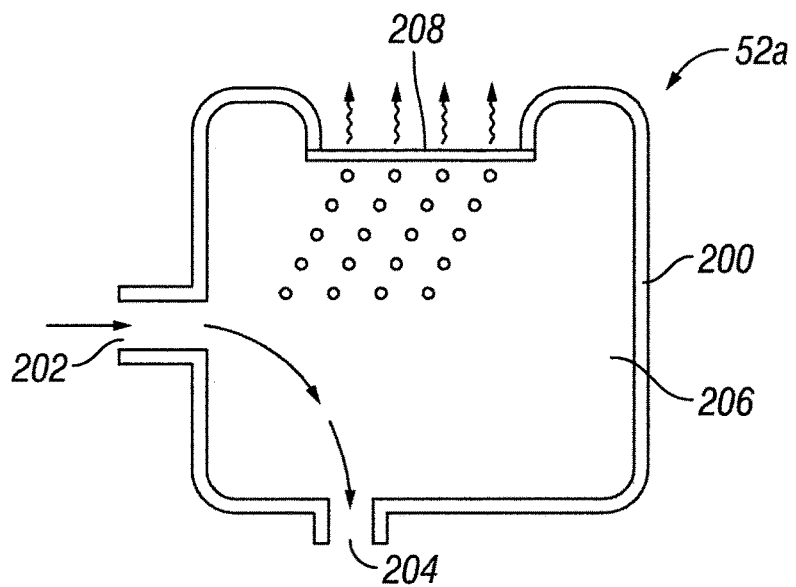
FIG. 8 is a cross sectional view of one non-limiting example of an air separator that may be useable in those embodiments of the present invention that have air separators.

The air separators 52 or 112 used in systems of the present invention may comprise any suitable types of air separating devices capable of removing bubbles or entrained air from liquid (and any sold or ice particles that may be present with the liquid as it passes through the air separator. FIG. 8 shows a non-limiting example of one type of air separator 52a that may be used. This air separator 52a comprises a housing 200 which defines an inner chamber 206 having an inlet port 202 and an outlet port 204. An air permeable member 208 (e.g., a filter) or open vent is located at the top of the housing. Heat exchange medium or slurry flows through inlet port 204 and pools in or flows through the inner chamber 204, where entrained air will rise to the top of the chamber 206 and escape through the air permeable member 208 or open vent. The remaining liquid or slurry will flow out of the outlet port 204. In some embodiments, the air will simply vent into the environment. In other embodiments, where indicated, a vent tuve or other conduit may be attached to the opening at the top of the housing 200 so that air which flows outwardly though the air permeable member 208 or open vent will be channeled through that vent tube or conduit to a desired location (see for example the embodiment of FIG. 4 where air from the air separator 52 is channeled through a vent tube 102 and used to drive a piston of an injector device 100.

Figure 9A:
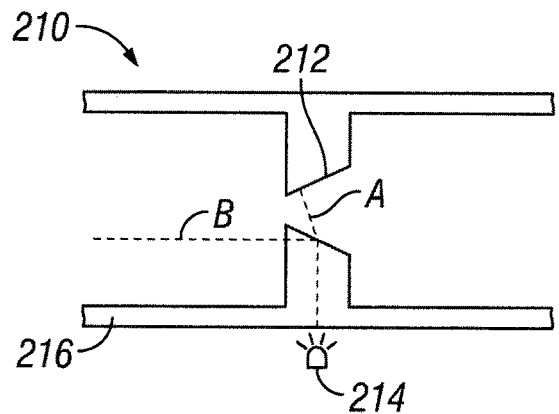
FIG. 9A is a schematic diagram of one non-limiting type of a liquid/gas/solid detector that may optionally be incorporated into any of the systems of the present invention to measure the relative amounts of liquid phase matter (e.g., saline solution), solid phase matter (e.g., frozen particles) and gas (e.g., air bubbles).
Figure 9B:
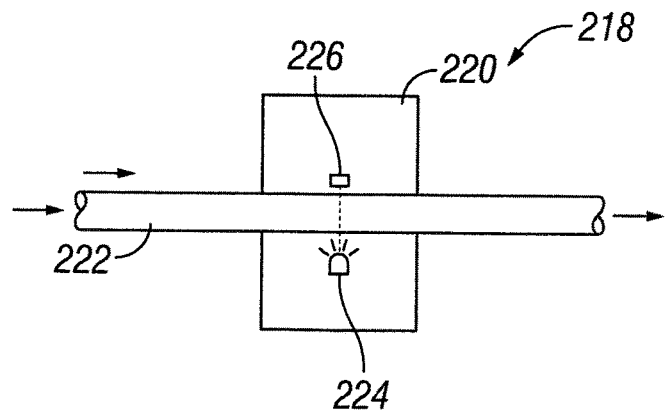
FIG. 9B is a schematic diagram of one non-limiting type of a liquid/gas/solid detector that may optionally be incorporated into any of the systems of the present invention to measure the relative amounts of liquid phase matter (e.g., saline), solid phase matter (e.g., frozen particles) and gas (e.g., air bubbles).

FIGS. 9A and 9B show sensors that may be used at various locations in any system of the present invention to sense the presence or absence of heat exchange medium and/or to sense the relative amounts of solid phase and liquid phase matter in slurry being circulated through the system Specifically, FIG. 9A shows a level sensor 210 of a type known in the art, which may be used to sense the level of heat exchange fluid in any tank, vessel, cassette, heat exchanger or other collection chamber of the system. In this sensor 210, light leaves an emitter/detector 214 located underneath a prism that may be molded into the wall 216 of the tank, vessel, cassette, heat exchanger or other collection chamber. If the tank, vessel, cassette, heat exchanger or other collection chamber is full of liquid, light transmits through the prism (refracting slightly) along path A, reflects off of a mirror, and travels back down through the prism where it is received by the detector element of the emitter/detector 214. If the tank, vessel, cassette, heat exchanger or other collection chamber reservoir is empty, light reflects off of the 45 degree angled surface 212 of the prism along path B, thereby causing the light to be scattered around the tank, vessel, cassette, heat exchanger or other collection chamber such that substantially no light returns to the detector element of the emitter/detector 214. If the reservoir contains liquid/ice slurry, light will reflect off of the ice particles, resulting in a moderate level of transmittance to the detector element of the emitter/detector 214.

FIG. 9B shows a sensor 218 that comprises a clamp 220 (off the shelf or custom) which goes around the outer diameter of a clear tube 222. Infrared light leaves an emitter 224 and enters the clear tube wall. If the tube is full of saline/water/liquid, the light transmits straight through the tube and on to the detector 226. If the tube contains air, some of the light will reflect off the tube wall, resulting in a low level of transmittance to the detector. If the tube contains a liquid/ice slurry, some of the light will reflect off of the ice particles, resulting in a moderate level of transmittance to the detector. Thus, one or more of these sensors 218 may be used to sense the amount of solid phase matter (e.g., ice) present in heat exchange fluid flowing through one or more tubes of the system.

The amount of solid phase matter in the heat exchange slurry may vary depending on the lumen size(s), heat exchanger configurations and flow restrictions inherent in design of the particular heat exchange catheter being used. Table 1 below shows examples of slurry concentrations, flow rates and resultant rates of solid phase matter delivery for several commercially available heat exchange catheters:

TABLE 1

| Commercially Available Catheter Example | Flow Rate of Heat Exchange Medium Through Catheter | Concentration of Solid Phase Matter (e.g., Ice) in Heat Exchange Slurry | Resultant Rate of Delivery of Solid Phase Matter (e.g., Ice) |
|---|---|---|---|
| Quattro ® (ZOLL Circulation, Sunnyvale, CA) | 200 mL/min | 50% | 100 g/min |
| Radiant GTO ® (ZOLL Circulation, Sunnyvale, CA) | 900 mL/min | 11% | 100 g/min |
| Solex/ICY ® (ZOLL Circulation, Sunnyvale, CA) | 200 mL/min | 18% | 35 g/min |

Thus, for these particular heat exchange catheters, the concentration of solid phase matter within the heat exchange slurry may range from about 18% by weight to about 50% by weight and the flow rate of the heat exchange slurry through the catheter may vary from about 200 mL/min (for relatively small catheters) to about 900 mL/min (for a relatively large catheter).

Although the examples shown in the drawings and described above are specific to heat exchange catheters wherein the at least a portion of the solid phase matter melts as it circulates through the catheter, it is to be appreciated that the invention is also useable in connection with body cooling devices other than catheters (e.g., cooling blankets, pads and other surface cooling devices through which a heat exchange medium is circulated. Also, it is to be appreciated that the solid phase matter need not necessarily melt while it is within the catheter or other body cooling device. Indeed, the melting of solid phase matter anywhere within the heat exchange medium flow path—even in an extracorporeal portion of the flow path—will enhance the removal of heat from the heat exchange medium. The energy transfer (Q) through the heat exchanger is dependent on three factors:
1) the heat transfer coefficient (h) of the exchanger,
2) the amount of surface area (A) available for heat transfer, and
3) the difference in temperature (ΔT) between the heat exchange medium circulating through the heat exchanger and the blood or other body fluid circulating through the subject's body in heat exchange proximity to the heat exchanger.

This may be mathematically expressed as follows:

$$Q = h * A * \Delta T$$

Increasing the efficiency or size of the heat exchanger (h and A), generally speaking, requires increasing the cost of the heat exchanger. In embodiments where the heat exchanger is part of a sterile, disposable catheter intended for disposal after a single use, substantial increases in cost may be undesirable. Therefore, the present invention provides a more cost-effective means of increasing energy transfer through the heat exchanger by effecting a solid to liquid phase change within the heat exchange medium, thereby enhancing the removal of heat from the heat exchange medium and resulting in a greater ΔT. To effect this solid to liquid phase change, solid phase matter must be created or introduced in the heat exchange medium in a manner that does not result in clogging or fowling of the system. The examples described above avoid problems of ice clogging or fowling flow. For example, in embodiments which employ a slurry-generating device or slurry source within the extracorporeal portion of the heat exchange fluid recirculation flow path, ice particles are introduced into the flowing heat exchange fluid and at least some of those ice particles subsequently melt somewhere downstream of the location at which they were introduced. In this way, ice particles act as a heat transport mechanism, effectively increasing the surface area of the cold source and subsequently undergoing a solid to liquid phase change. This achieves greater heat transfer and more efficient and rapid cooling of the subject's body than traditional heat exchange catheter systems circulating liquid phase heat exchange fluid which cannot have an initial temperature less than 0 C.

The invention has been described hereabove with reference to certain examples or embodiments of the invention. No attempt has been made to exhaustively describe all possible embodiments and examples of the invention. Indeed, various additions, deletions, alterations and modifications may be made to the above described examples and embodiments without departing from the intended spirit and scope of the invention. For example, any element or attribute of one embodiment or example may be incorporated into or used with another embodiment or example, unless to do so would render the embodiment or example unsuitable for its intended use. Also, where the steps of a method or process are described, listed or claimed in a particular order, such steps may be performed in any other order unless to do so would render the embodiment or example un-novel, obvious to a person of ordinary skill in the relevant art or unsuitable for its intended use. All reasonable additions, deletions, modifications and alterations are to be considered equivalents of the described examples and embodiments and are to be included within the scope of the following claims.

What is claimed is:

1. A system comprising:
a heat exchange catheter that is sized to be insertable into or positionable within a blood vessel of a subject and useable to exchange heat with blood flowing through the blood vessel, said heat exchange catheter having a closed loop heat exchange medium recirculation path comprising an endovascular heat exchanger, an inflow lumen and an outflow lumen, said endovascular heat exchanger being configured to allow heat exchange between a heat exchange medium and the blood flowing through the blood vessel without causing the heat exchange medium to directly contact or mix with body fluid or tissue of a body of the subject;
an inflow conduit connectable to the inflow lumen of the heat exchange catheter;
an outflow conduit connectable to the outflow lumen of the heat exchange catheter;
a pump or pressurization apparatus for recirculating the heat exchange medium through the inflow conduit, through the inflow lumen, through the endovascular heat exchanger, through the outflow lumen, out of the outflow conduit and back into the inflow conduit while the heat exchange catheter is inserted in the blood vessel;
a disposable slurry generator configured for creating solid phase matter in, or adding solid phase matter to, the heat exchange medium, as needed, such that the heat exchange medium includes a desired concentration of the solid phase matter for circulating into the heat exchange catheter, wherein the disposable slurry generator comprises a vessel in which the solid phase matter is created or added to the heat exchange medium, the vessel being separated from a recirculating tube that bypasses the vessel;
wherein an amount of the solid phase matter melts as the solid phase matter circulates through the endovascular heat exchanger and exchanges heat with blood circulating through the blood vessel in which the endovascular heat exchanger is positioned;
wherein the endovascular heat exchanger is constructed, and the pump or pressurization apparatus is operative, such that during recirculation of the heat exchange medium through the endovascular heat exchanger within the subject's blood vessel, a diameter of the endovascular heat exchanger remains smaller than a diameter of the blood vessel in which the endovascular heat exchanger is positioned so that blood continues to flow through the blood vessel and past the endovascular heat exchanger;
at least one sensor configured to sense an amount of the solid phase matter that remains in the heat exchange medium after the heat exchange medium is circulated through the endovascular heat exchanger, and;

a controller that receives sensor signals from said at least one sensor, the controller being configured to control flow of the heat exchange medium from each of the vessel and from the recirculating tube that bypasses the vessel to cause adjustment of an amount of the solid phase matter added to the heat exchange medium and a desired concentration of solid phase matter in the heat exchange medium for recirculating back into the inflow lumen of the heat exchange catheter.

2. The system according to claim 1 wherein the disposable slurry generator for creating the solid phase matter in or adding the solid phase matter to the heat exchange medium comprises:
   a freezer device which causes partial freezing of the heat exchange medium thereby creating particles of solid phase matter in the heat exchange medium.

3. The system according to claim 2 wherein the disposable slurry generator for creating the solid phase matter in or adding the solid phase matter to the heat exchange medium comprises:
   a device for adding particles of the solid phase matter to the heat exchange medium.

4. The system according to claim 3 wherein the device for adding the solid phase matter to the heat exchange medium comprises a device for combining a slurry concentrate with the heat exchange medium.

5. The system according to claim 1 wherein the heat exchange medium is sterile.

6. The system according to claim 1, wherein the solid phase matter is selected from the group consisting of:
   frozen saline solution; and
   ice.

7. The system according to claim 2 wherein the freezer device is configured to cause partial freezing of the heat exchange medium after the heat exchange medium has returned from the endovascular heat exchanger and before the heat exchange medium re-circulates back into the endovascular heat exchanger.

8. The system according to claim 3 wherein the device for adding particles of the solid phase matter to the heat exchange medium is configured to add the particles of solid phase matter to the heat exchange medium after the heat exchange medium has returned from the heat exchange catheter and before the heat exchange medium recirculates back into the heat exchange catheter.

9. The system according to claim 8 wherein the device for adding particles of solid phase matter to the heat exchange medium comprises an upstream check valve, a downstream check valve, a compressible diaphragm and a ram that repeatedly compresses and decompresses the compressible diaphragm thereby causing a desired amount of slurry concentrate to be added to the heat exchange medium.

10. The system according to claim 1 wherein the desired concentration of solid phase matter is greater than about 50%.

11. The system according to claim 1 wherein the desired concentration of solid phase matter is from about 18% to 50%.

12. The system according to claim 4 wherein the device for combining a slurry concentrate with the heating exchange medium is configured to remove a volume of gas phase and liquid phase matter that is present in the heat exchange medium and to replace that removed volume with an equivalent volume of the slurry concentrate.

13. The system according to claim 2 wherein the freezer device comprises an in-line freezer that creates ice particles in the heat exchange medium.

14. The system according to claim 1 wherein the heat exchange medium includes a liquid phase matter which comprises a sterile solution suitable for intravenous administration.

15. The system according to claim 1 wherein the heat exchange medium includes a liquid phase matter, which is selected from the group consisting of:
   saline solutions;
   aqueous 0.9% NaCl solution; and
   water.

16. A system according to claim 7 wherein the apparatus for diluting comprises a conduit that delivers re-circulated heat exchange medium which has previously circulated through the catheter, wherein at least some of the solid phase matter has melted.

17. A system according to claim 16 further comprising a temperature sensor for sensing the temperature of the re-circulated heat exchange medium.

18. A system according to claim 16 further comprising an extracorporeal heat exchanger which alters the temperature of the re-circulated heat exchange medium.

19. A system according to claim 18 wherein the extracorporeal heat exchanger alters the temperature of the re-circulated heat exchange medium before it becomes combined with the heat exchange medium concentrate.

20. A system according to claim 16 further comprising an air separator which removes air from the re-circulated heat exchange medium.

21. A system according to claim 1 wherein the heat exchange medium source comprises a device that generates the heat exchange medium.

22. A system accordin to claim 21 wherein the device that generates the heat exchange medium comprises a slurry generating device.

23. A system according to claim 22 wherein the slurry generating device comprises:
   a vessel having an inlet, an outlet, at least one wall having an inner surface and a scraping device for scraping frozen matter from the inner wall; and
   chilling apparatus for chilling the wall of the vessel.

24. A system according to claim 23 wherein the vessel is disposable and the chilling apparatus is reuseable.

25. A system according to claim 23 wherein the chilling apparatus comprises first and second chilling members that are alternately positionable in a) a spaced apart configuration that allows removal of one vessel and insertion of a new vessel to a location between the chilling member and b) a closed configuration where the chilling members are in contact with or close to at least one wall of the vessel.

26. A system according to claim 23 wherein the vessel has a frustoconical configuration and wherein the chilling apparatus has a tapered receiving area into which the vessel is insertable and from which the vessel is removable.

27. A system according to claim 23 wherein the inlet of the vessel is connected to a line that carries a slow of fluid comprising re-circulated heat exchange medium that has previously passed through the catheter, wherein at least some of the solid phase particles have melted.

28. The system according to claim 1 wherein the heat exchange catheter has a heat exchange region where most heat exchange occurs, the heat exchange region being discrete.

29. The system according to claim 28 wherein the heat exchange region is non-expandable and remains at substantially a same diameter during insertion and use.

30. The system according to claim 29 wherein the heat exchange region is formed at least in part of a heat transferring material selected from the group consisting of: polymers, metals, ceramics, polymer-metal composites, polymer metal mixtures, ceramic-metal composites and ceramic-metal mixtures.

31. The system according to claim 30 wherein the heat exchange region comprises a metalized ceramic material.

32. The system according to claim 28 wherein the heat exchange region is expandable.

33. The system according to claim 32 wherein the heat exchange region comprises a balloon.

34. The system according to claim 32 wherein the heat exchange region of the heat exchange catheter is disposable in a non-expanded configuration during insertion and subsequently expandable to an expanded configuration, wherein the expanded configuration has a greater heat exchange surface area than the non-expanded configuration.

35. The system according to claim 34 wherein the heat exchange region comprises a balloon structure which has a first circumscribed diameter D1 when in a non-expanded configuration and a second circumscribed diameter D2 when in an expanded configuration.

36. The system according to claim 1 wherein the endovascular heat exchanger comprises a plurality of tubular, helically shaped, balloon elements through which the heat exchange medium circulates.

37. The system according to claim 1 further comprising a body temperature sensor that communicates with the controller, wherein the controller is configured to cause the one or more components to discontinue inclusion of the solid phase matter in the heat exchange medium after initial lowering of the subject's body temperature to a desired hypothermic temperature.

38. The system of claim 1, wherein the pump is a first pump, the system further comprising a second pump, wherein the controller is configured to control each of the first pump and the second pump to cause a ratio of a first portion of the heat exchange medium from the vessel of the slurry generator and a second portion of the heat exchange medium recirculated from the heat exchange catheter, the ratio of the first portion and the second portion configured to cause the desired concentration of the solid phase matter for circulating into the heat exchange catheter.

* * * * *